United States Patent
Fine et al.

(10) Patent No.: US 10,960,168 B2
(45) Date of Patent: Mar. 30, 2021

(54) DELIVERY OF HIGH CONCENTRATION NITRIC OXIDE

(75) Inventors: David H. Fine, Cocoa Beach, FL (US); Lee Leichter, Fort Myers, FL (US)

(73) Assignee: VERO Biotech LLC, Atlanta, GA (US)

( * ) Notice: Subject to any disclaimer, the term of this patent is extended or adjusted under 35 U.S.C. 154(b) by 0 days.

(21) Appl. No.: 12/541,148

(22) Filed: Aug. 13, 2009

(65) Prior Publication Data
US 2010/0089392 A1  Apr. 15, 2010

Related U.S. Application Data

(60) Provisional application No. 61/090,628, filed on Aug. 21, 2008.

(51) Int. Cl.
| | |
|---|---|
| *A61M 16/12* | (2006.01) |
| *A61M 15/00* | (2006.01) |
| *A61K 31/04* | (2006.01) |
| *A61P 11/00* | (2006.01) |

(52) U.S. Cl.
CPC .............. *A61M 16/12* (2013.01); *A61K 31/04* (2013.01); *A61M 15/008* (2014.02); *A61P 11/00* (2018.01); *A61M 15/0071* (2014.02); *A61M 2202/0208* (2013.01); *A61M 2202/0275* (2013.01); *A61M 2205/8225* (2013.01); *A61M 2205/8231* (2013.01)

(58) Field of Classification Search
CPC .... A61M 16/00; A61M 16/10; A61M 16/104; A61M 16/12; A61M 2016/00; A61M 2016/10; A61M 2016/1005; A61M 2016/102; A61M 2016/1035; A61M 2016/12; A61M 2016/122; A61M 2016/125

USPC ............ 128/202.26, 203.12, 203.22, 204.14, 128/204.18, 205.25
See application file for complete search history.

(56) References Cited

U.S. PATENT DOCUMENTS

| | | | | |
|---|---|---|---|---|
| 5,570,683 | A * | 11/1996 | Zapol .................. | 128/200.14 |
| 5,651,358 | A * | 7/1997 | Briend et al. .......... | 128/203.12 |
| 5,918,596 | A * | 7/1999 | Heinonen .............. | 128/204.21 |
| 6,142,147 | A | 11/2000 | Head et al. | |
| 6,581,599 | B1 * | 6/2003 | Stenzler .............. | 128/204.23 |

(Continued)

FOREIGN PATENT DOCUMENTS

| | | |
|---|---|---|
| EP | 0 960 629 | 12/1999 |
| JP | H10-179742 | 7/1998 |

(Continued)

OTHER PUBLICATIONS

Miller, Celermajer, Deanfield, Macrae. Guidelines for the safe administration of inhaled nitric oxide. 1994. Archives of Disease in Childhood. 70. F47-F49.*

(Continued)

*Primary Examiner* — Valerie L Woodward

(57) ABSTRACT

A method and device can alternately deliver high concentration of nitric oxide and oxygen-enriched air. A method of providing a therapeutic amount of nitric oxide to a mammal can include delivering one or more breaths of a therapeutic amount of nitric oxide to the mammal and delivering one or more breaths of an amount of oxygen-enriched air to the mammal immediately after the one or more breaths of the therapeutic amount of nitric oxide.

11 Claims, 2 Drawing Sheets

(56) References Cited

U.S. PATENT DOCUMENTS

| | | | |
|---|---|---|---|
| 7,861,717 B1* | 1/2011 | Krebs | 128/204.23 |
| 2006/0048779 A1 | 3/2006 | Rounbehler et al. | |
| 2006/0180147 A1* | 8/2006 | Rounbehler et al. | 128/203.12 |
| 2006/0207594 A1 | 9/2006 | Stenzler et al. | |
| 2006/0278224 A1* | 12/2006 | Shaffer et al. | 128/204.26 |
| 2007/0144515 A1* | 6/2007 | Stenzler et al. | 128/203.25 |
| 2008/0029093 A1 | 2/2008 | Stenzler et al. | |
| 2008/0193566 A1* | 8/2008 | Miller | A61P 9/12 424/718 |
| 2010/0018526 A1* | 1/2010 | Miller et al. | 128/203.12 |

FOREIGN PATENT DOCUMENTS

| | | |
|---|---|---|
| JP | 2000-79166 A | 3/2000 |
| JP | 2004-275706 A | 10/2004 |
| JP | 2007-537267 | 12/2007 |
| JP | 2008-510675 | 4/2008 |
| WO | WO 1992/010228 | 6/1992 |
| WO | WO 2005/110441 | 11/2005 |
| WO | WO 2006/023616 | 3/2006 |
| WO | WO 2006/090260 | 8/2006 |
| WO | WO 2007/037975 | 4/2007 |
| WO | WO 2010/021943 | 2/2010 |
| WO | WO 2010021941 | 2/2010 |

OTHER PUBLICATIONS

Examination Report No. 1 for Australian Application No. 2009282987, dated May 20, 2014, 3 pages.
Office Action for Canadian Application No. 2,734,727, dated Jun. 1, 2020, 5 pages.
Office Action for European Application No. 09808648.1, dated Mar. 19, 2013, 5 pages.
Office Action for European Application No. 09808648.1, dated Jan. 29, 2016, 4 pages.
Office Action for European Application No. 09808648.1, dated Jul. 6, 2017, 3 pages.
Notice of Reasons for Refusal for Japanese Application No. 2011-523892, dated Jul. 24, 2013, 6 pages.
Decision of Refusal for Japanese Application No. 2011-523892, dated Aug. 7, 2014, 7 pages.
Notice of Reasons for Refusal for Japanese Application No. 2014-249597, dated Dec. 24, 2015, 9 pages.
Decision of Refusal for Japanese Application No. 2014-249597, dated Nov. 29, 2016, 10 pages.
Notice of Reasons for Refusal for Japanese Application No. 2017-075034, dated Feb. 27, 2018, 13 pages.
Decision of Refusal for Japanese Application No. 2017-075034, dated Sep. 28, 2018, 6 pages.
Notice of Reasons for Refusal for Japanese Application No. 2019-021435, dated Jan. 22, 2020, 6 pages.
Notice of Reasons for Refusal for Japanese Application No. 2019-021435, dated Sep. 30, 2020, 6 pages.
International Search Report and Written Opinion for International Application No. PCT/US2009/053947, dated Oct. 13, 2009, 7 pages.
European supplementary search report for European Application No. 09808648.1 dated Jul. 17, 2012.

* cited by examiner

DELIVERY OF HIGH CONCENTRATION NITRIC OXIDE

CLAIM OF PRIORITY

This application claims the benefit of prior U.S. Provisional Application No. 61/090,628, filed on Aug. 21, 2008, which is incorporated by reference in its entirety.

TECHNICAL FIELD

This description relates to devices and methods for delivery of nitric oxide.

BACKGROUND

Nitric oxide (NO), also known as nitrosyl radical, is a free radical that is an important signaling molecule in pulmonary vessels. Nitric oxide (NO) can moderate pulmonary hypertension caused by elevation of the pulmonary arterial pressure. Inhaling low concentrations of nitric oxide (NO), for example, in the range of 2-100 ppm can rapidly and safely decrease pulmonary hypertension in a mammal by vasodilation of pulmonary vessels.

Some disorders or physiological conditions can be mediated by inhalation of nitric oxide (NO). The use of low concentrations of inhaled nitric oxide (NO) can prevent, reverse, or limit the progression of disorders which can include, but are not limited to, acute pulmonary vasoconstriction, traumatic injury, aspiration or inhalation injury, fat embolism in the lung, acidosis, inflammation of the lung, adult respiratory distress syndrome, acute pulmonary edema, acute mountain sickness, post cardiac surgery acute pulmonary hypertension, persistent pulmonary hypertension of a newborn, perinatal aspiration syndrome, haline membrane disease, acute pulmonary thromboembolism, heparin-protamine reactions, sepsis, asthma and status asthmaticus or hypoxia. Nitric oxide (NO) can also be used to treat chronic pulmonary hypertension, bronchopulmonary dysplasia, chronic pulmonary thromboembolism and idiopathic or primary pulmonary hypertension or chronic hypoxia.

SUMMARY

In one aspect, a method of providing a therapeutic amount of nitric oxide to a mammal includes delivering one or more breaths of a therapeutic amount of nitric oxide to the mammal and delivering one or more breaths of an amount of oxygen-enriched air to the mammal immediately after the one or more breaths of the therapeutic amount of nitric oxide. The method can further include alternating the delivery of nitric oxide and oxygen-enriched air to the mammal. The method can further include delivering one or more breaths of an amount of oxygen-enriched air to the mammal before delivering one or more breaths of a therapeutic amount of nitric oxide to the mammal. One breath of nitric oxide can be delivered for one to six seconds and one breath of oxygen-enriched air can be delivered for one to six seconds. The breaths of nitric oxide and oxygen-enriched air can be delivered to the mammal in a pre-determined delivery sequence. One breath of nitric oxide can be followed by one or more breaths of oxygen-enriched air. Two breaths of nitric oxide can be followed by two or more breaths of oxygen-enriched air. One breath of nitric oxide can be followed by multiple breaths of oxygen-enriched air. Two breaths of nitric oxide can be followed by multiple breaths of oxygen-enriched air. The method can further include generating nitric oxide by exposing nitrogen dioxide to an antioxidant. The antioxidant can be ascorbic acid, alpha tocopherol or gamma tocopherol. The oxygen-enriched air can contain at least 21% oxygen. The therapeutic amount of nitric oxide can be at least 2 ppm and as high as 2000 ppm.

In another aspect, a method of providing a therapeutic amount of nitric oxide to a mammal can include exposing the mammal to a therapeutic amount of nitric oxide for a first amount of time, and exposing the mammal to an amount of oxygen-enriched air for a second amount of time.

In another aspect, a device for intermittent delivery of nitric oxide can include a delivery tube configured to deliver nitric oxide containing gas, a delivery tube configured to deliver oxygen enriched gas and a patient interface coupled to the delivery device. The delivery tube configured to deliver nitric oxide containing gas can include a surface activated material saturated with an antioxidant. The antioxidant can be ascorbic acid, alpha tocopherol or gamma tocopherol. The nitric oxide containing gas can contain at least 2 ppm of nitric oxide. The oxygen enriched gas can contain at least 21% oxygen. The patient interface can be a mouth piece, nasal cannula, face mask or a fully-sealed face mask. The device can further include a switch controlling the delivery of NO between the delivery tube configured to deliver nitric oxide containing gas and the delivery tube configured to deliver oxygen enriched gas. The switch can be controlled manually. The switch can be controlled by a user or care giver. The switch can be controlled electronically through a computer.

In another aspect, a device for intermittent delivery of nitric oxide can include a single delivery tube configured to deliver nitric oxide containing gas, and a patient interface coupled to the delivery device. The patient interface can be a mouth piece, nasal cannula, face mask or a fully-sealed face mask.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
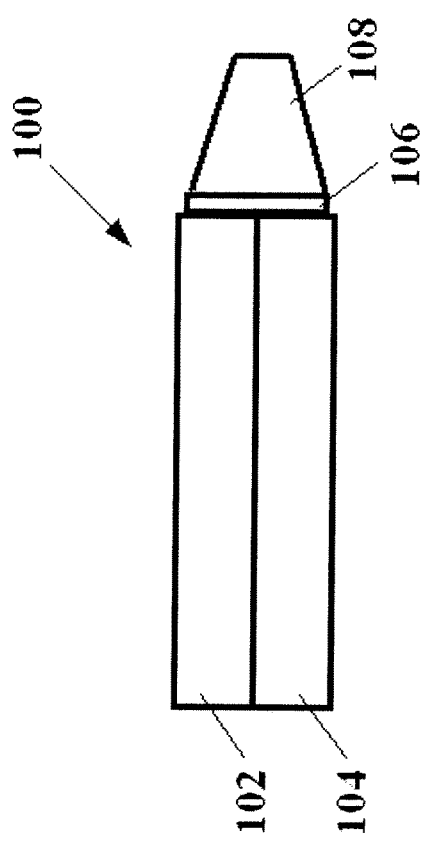
FIG. 1 is a block diagram of one embodiment of a NO delivery device.

There are several potential patient risks associated with the delivery of high concentrations of NO. These risks include the formation of Nitrogen Dioxide ($NO_2$), a toxic byproduct formed through the oxidation of NO when mixed with Oxygen ($O_2$). A second patient risk is the formation of high levels of methemoglobin when high concentrations of NO interact with heme in the blood, causing methemoglobinemia. Finally, prolonged continuous inhalation of NO can cause a "rebound" effect in some patients which causes an increase in pulmonary pressure when the NO is abruptly discontinued, requiring a prolonged weaning. This effect is thought to be due to the lowered production of endogenous NO after prolonged delivery of exogenous NO. Accordingly, there remains a need for safe delivery of high concentrations of NO to an individual.

There is evidence that very high levels of NO (up to 1000 to 2000 ppm) are routinely inhaled during the inhalation of cigarette smoke, where the last puff can contain NO levels of this magnitude. Although the toxic and long term effects of smoking are well known, there does not seem to be any acute toxic reactions such as including methemoglobinemia, $NO_2$ exposure or a rebound effect (increased pulmonary pressure) to these levels of NO when the smoking is discontinued.

In one embodiment, safe delivery of high concentrations of NO to a mammal can be achieved via a pulsed or intermittent or alternate delivery of therapeutic NO in a discontinuous manner that is interspersed with breaths of oxygen containing gas or ambient air. Such a method reduces the potential toxic reactions listed above as compared to continuous delivery of lower levels of NO mixed with oxygen.

The delivery of NO to a mammal can be accomplished through delivery of one or more breaths of a NO containing gas followed by one or more breaths of an oxygen containing gas capable of sustaining respiration. In one embodiment, the method of providing a therapeutic amount of nitric oxide to a mammal includes delivering one or more breaths of a therapeutic amount of nitric oxide to the mammal and delivering one or more breaths of an amount of oxygen-enriched air to the mammal immediately after the one or more breaths of the therapeutic amount of nitric oxide. The method can further include alternating the delivery of nitric oxide and oxygen-enriched air to the mammal. The method can further include delivering one or more breaths of an amount of oxygen-enriched air to the mammal before delivering one or more breaths of a therapeutic amount of nitric oxide to the mammal. One breath of nitric oxide can be delivered for one to six seconds and one breath of oxygen-enriched air can be delivered for one to six seconds.

In one embodiment, the NO gas can be inhaled by an individual for a few seconds up to as long as several minutes. In one embodiment, the NO gas can be inhaled for 1, 5, 10, 15, 20, 25, 30, 35, 40, 45, 50, 55 or 60 seconds. In another embodiment, the NO gas can be inhaled for 1, 2, 3, 4 or 5 minutes. In another embodiment, the NO gas can be inhaled for 1, 2, 3, 4, 5 or 10 breaths. This can be followed by the inhalation of $O_2$ containing gas for a few seconds up to as long as several minutes to several hours. In one embodiment, the $O_2$ containing gas can be inhaled for 1, 5, 10, 15, 20, 25, 30, 35, 40, 45, 50, 55 or 60 seconds. In another embodiment, the $O_2$ containing gas can be inhaled for 1, 2, 3, 4, 5, 10, 20, 30, 60 or more minutes. In another embodiment, the $O_2$ containing gas can be inhaled for 1, 2, 3, 4, 5, 10, 20, 30, 60, 100, 1000 or more breaths.

In an alternative embodiment, the breaths of nitric oxide and oxygen-enriched air can be delivered to the mammal in a pre-determined delivery sequence. For example, one breath of nitric oxide (NO) can be followed by one breath of oxygen-enriched ($O_2$) air. Alternatively, two breaths of nitric oxide can be followed by one breath of oxygen-enriched air. Alternatively, one breath of nitric oxide can be followed by two breaths of oxygen-enriched air. Alternatively, two breaths of nitric oxide can be followed by two breaths of oxygen-enriched air. Other combinations of a pre-determined delivery sequence can include but are not limited to the following: NO, NO, NO, $O_2$, NO, NO, NO . . . ; NO, NO, $O_2$, $O_2$, $O_2$, NO, NO, . . . ; NO, $O_2$, $O_2$, $O_2$, NO, $O_2$, $O_2$, $O_2$, . . . ; NO, NO, NO, $O_2$, $O_2$, $O_2$, . . . ; NO, NO, NO, NO, $O_2$, NO, NO, NO, NO, . . . ; NO, NO, NO, NO, $O_2$, $O_2$, NO, NO, NO, NO, . . . ; NO, NO, NO, NO, $O_2$, $O_2$, $O_2$, NO, NO, NO, NO, . . . ; NO, NO, NO, NO, $O_2$, $O_2$, $O_2$, $O_2$, NO, NO, NO, NO, . . . ; or another combination suitable for the condition being treated.

According to one embodiment, NO gas having a concentration of approximately 2 to approximately 1000 ppm (e.g. greater than 2, 10, 20, 40, 80, 100, 150, 200, 250, 300, 350, 400, 450, 500, 550, 600, 650, 700, 750, 800, 850, 900, 1000 or 2000 ppm) can be delivered. The NO containing gas can be mixed with $N_2$, air or any $O_2$ containing gas. The $O_2$ containing gas can be ambient air that contains a concentration of approximately 21% to 100% $O_2$.

A pulsed or intermittent NO delivery system is provided. The delivery device can be self-contained, portable systems that do not require heavy gas bottles, sophisticated electronics or monitoring equipment. The delivery devices are easy to use and do not require any specialized training. The delivery devices allow an individual to self-administer the pulsed or intermittent NO treatment. The pulsed or intermittent NO delivery system can be sized to be readily transportable for emergency use or to be kept by patients who are in need of emergency therapeutic doses of NO for use whenever needed. The NO delivery system can also be used to deliver NO to a patient in a medical setting such as a hospital, ambulance or medical clinic. In one embodiment, the NO delivery system can be designed for a one-time use. In another embodiment, the NO delivery system can be designed for short term treatments.

In one embodiment, the delivery system can include two separate delivery tubes, one delivery tube configured to deliver NO containing gas and a second delivery tube configured to deliver an $O_2$ containing gas capable of sustaining respiration. In another embodiment, the pulsed or intermittent delivery of NO can be achieved by a single delivery tube configured to deliver NO containing gas. In such an embodiment, the alternate non-NO containing breaths can be taken from the ambient air.

The switch between the two sources of gas in the delivery system that includes two separate delivery tubes can be manually affected by the user or care giver (bolus delivery), or mechanically controlled using a counter or electronically controlled through use of a programmable CPU. The switch can be a valve that controls the flow of gases.

The delivery tubes can be a gas bottle containing an appropriate amount of $NO_2$ in oxygen or air attached to a NO generation cartridge, which converts $NO_2$ in the gas bottle into a therapeutic amount of NO gas. In one embodiment, opening the valve on the gas bottle can provide an instant source of NO in air or oxygen if the gas bottle contains $NO_2$ in air or oxygen and the gas first flows through a antioxidant cartridge to convert the $NO_2$ to NO. NO can be delivered in a carrier gas such as air, pure oxygen, or some oxygen concentration in between the oxygen concentration in air and pure oxygen. In one embodiment, the carrier gas is $O_2$ at about 90 to 99.9%.

Alternatively, the delivery tube can be a miniaturized gas bottle, similar to an aerosol can, attached to a miniaturized NO generation cartridge. In another embodiment, the delivery tube can be an inhaler that delivers a therapeutic amount of NO gas ranging from 2 to 2000 ppm. The delivery tube configured to deliver NO containing gas can further include a surface-active material coated with an aqueous solution of antioxidant as a simple and effective mechanism for converting any $NO_2$ to NO. More particularly, $NO_2$ can be converted to NO by passing the dilute gaseous $NO_2$ over a surface-active material coated with an aqueous solution of antioxidant. The antioxidant can be ascorbic acid, alpha tocopherol or gamma tocopherol.

As shown in FIG. 1, the NO delivery device 100 includes a delivery tube configured to deliver NO containing gas 102 and a second delivery tube containing an $O_2$ containing gas capable of sustaining respiration 104. The NO delivery device also includes a switch 106 to allow the patient to take several breaths from the delivery tube configured to deliver NO containing gas 102 before closing off the gas flow from the delivery tube containing NO containing gas 102 and allowing the patient to take several breaths from the delivery tube configured to deliver an $O_2$ containing gas 104. The delivery tube configured to deliver NO containing gas can store a therapeutic amount of $NO_2$ that is converted into NO. The therapeutic amount of NO can be diluted to the necessary concentration and stored with nitrogen, air, oxygen enriched air or substantially pure oxygen. In another embodiment, the therapeutic amount of NO is not diluted. A patient interface 108 can be directly coupled to the delivery tubes. The delivery tubes can be configured to receive gas tube plumbing (or other conduits known or developed in the art) that includes a mouth piece, nasal cannula, face mask or fully-sealed face mask. In one embodiment, a NO generation cartridge can be directly coupled to (and detachable from) a patient interface 108. In another embodiment, the switch 106 can be mechanically controlled using a counter or electronically controlled though the use of a programmable CPU.

Figure 2:
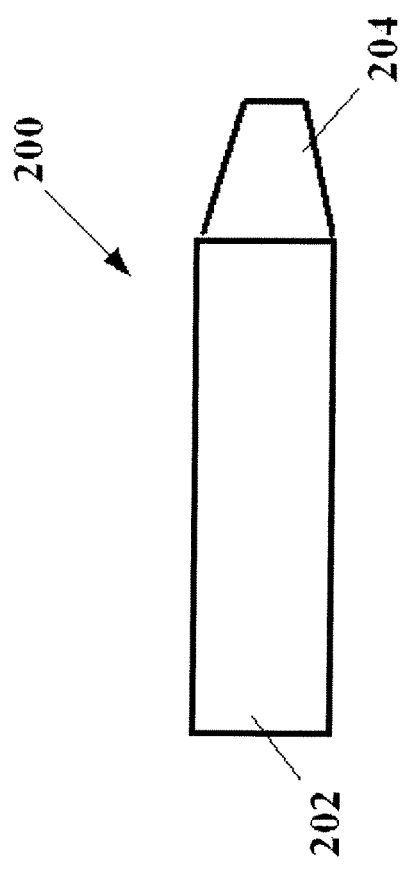
FIG. 2 is a block diagram of another embodiment of a NO delivery device.

FIG. 2 illustrates another embodiment of a NO delivery device. As shown in FIG. 2, the NO delivery device 200 includes a single delivery tube configured to deliver NO containing gas 202. A patient interface 204 can be directly coupled to the delivery tube. The delivery tube 202 can be configured to receive gas tube plumbing (or other conduits known or developed in the art) that includes a mouth piece, nasal cannula, face mask or fully-sealed face mask. In one embodiment, a NO generation cartridge can directly coupled to (and detachable from) a patient interface 204.

Figure 3:
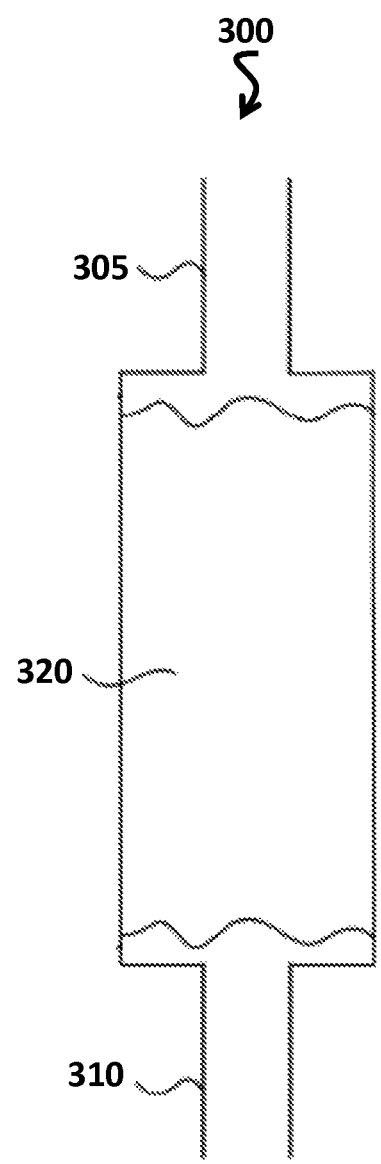
FIG. 3 is a block diagram of a cartridge that converts $NO_2$ to NO.

FIG. 3 illustrates an embodiment of a NO generation cartridge that generates NO from $NO_2$. The cartridge 300, which may be referred to as a NO generation cartridge, a GENO cartridge, or a GENO cylinder, includes an inlet 305 and an outlet 310. A porous screen is located at both the inlet 305 and the outlet 310, and the remainder of the cartridge 300 is filled with a surface-active material 320 that is soaked with a saturated solution of antioxidant in water to coat the surface-active material. In the example of FIG. 3, the antioxidant is ascorbic acid.

Other implementations are within the scope of the following claims.

What is claimed is:

1. A method, comprising:
   repeatedly delivering, for periods of at least two breaths, between 1000 ppm and 2000 ppm of nitric oxide to a mammal; and
   delivering, between each period, at least one breath of oxygen-enriched air to the mammal.

2. The method of claim 1, further comprising delivering one or more breaths of the oxygen-enriched air to the mammal before delivering the at least two breaths of nitric oxide to the mammal.

3. The method of claim 1, wherein:
   one breath of the oxygen-enriched air is delivered between each period.

4. The method of claim 1, wherein:
   each period of delivery of nitric oxide has a duration of two breaths; and
   two breaths of the oxygen-enriched air are delivered between each period.

5. The method of claim 1, further comprising generating the nitric oxide by exposing nitrogen dioxide to an antioxidant.

6. The method of claim 5, wherein the antioxidant is at least one of ascorbic acid, alpha tocopherol, or gamma tocopherol.

7. The method of claim 5, wherein the nitric oxide is delivered to the mammal via a tube that includes the antioxidant.

8. The method of claim 7, wherein the antioxidant is at least one of ascorbic acid, alpha tocopherol, or gamma tocopherol.

9. The method of claim 1, wherein the balance of the between 1000 ppm and 2000 ppm of nitric oxide is air.

10. The method of claim 1, wherein oxygen enriched air contains at least 21% oxygen.

11. The method of claim 1, wherein:
   the nitric oxide is delivered to the mammal via a first tube; and
   the oxygen-enriched air is delivered to the mammal via a second tube different from the first tube.

* * * * *